United States Patent [19]

Bettarini et al.

[11] Patent Number: 5,169,848
[45] Date of Patent: Dec. 8, 1992

[54] PYRIDAZINONES ENDOWED WITH INSECTICIDAL AND ACARICIDAL ACTIVITY

[75] Inventors: Franco Bettarini; Luigi Capuzzi, both of Novara; Sergio Massimini, Bollate; Paolo Castoro, Vercelli; Vincenzo Caprioli, Pavia, all of Italy

[73] Assignee: Presidenza del Consiglio dei Ministri-Ufficio del Ministro per il coordinamento delle iniziative per la ricerva Scientifica e Tecnologica, Rome, Italy

[21] Appl. No.: 504,020

[22] Filed: Apr. 4, 1990

[30] Foreign Application Priority Data

Apr. 5, 1989 [IT] Italy ................. 20013 A/89

[51] Int. Cl.$^5$ .................. C07D 237/16; A01G 43/58
[52] U.S. Cl. .................. 514/247; 514/252; 544/238; 544/240
[58] Field of Search ............. 544/240, 238; 514/247, 514/252

[56] References Cited

U.S. PATENT DOCUMENTS 4,837,217  6/1989  Octura et al. .............. 514/252
4,910,201  3/1990  Kawamura ................ 544/240

FOREIGN PATENT DOCUMENTS 1017570   1/1986  Japan ................ 514/247
1112057   5/1986  Japan ................ 514/247
0275569  11/1988  Japan ................ 544/238

Primary Examiner—Donald G. Daus
Attorney, Agent, or Firm—Stevens, Davis, Miller & Mosher

[57] ABSTRACT

Pyridazinones endowed with insecticidal and acaricidal activity are disclosed, which have the general formula:

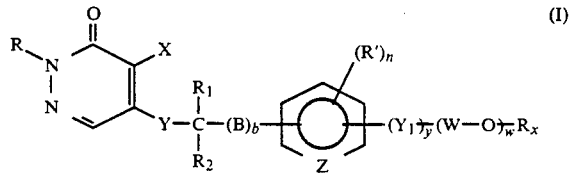

wherein the symbols have the meaning as defined in claim 1.

27 Claims, No Drawings

PYRIDAZINONES ENDOWED WITH INSECTICIDAL AND ACARICIDAL ACTIVITY

DESCRIPTION OF THE INVENTION

The present invention relates to novel derivatives of 3(2H)-pyridazinone, to the processes for preparing them, to the insecticidal and acaricidal compositions which contain the novel compounds, and to the use of said compositions for the control of insects, mites and ticks.

Compounds belonging to the class of 3(2H)-pyridazinones and displaying fungicidal, insecticidal, acaricidal and nematocidal activity are disclosed in European patent applications 88,384; 134,439; 183,212; 199,281; 232,825.

The present invention relates in particular to a novel class of substituted pyridazinones endowed with an increased efficacy in the control, in particular, of harmful mites in the agricultural, civil and zootechnical fields.

In fact, pyridazinones of general formula (I), as defined herein in the following, containing in their molecule specific halogenated moieties $$-(Y_1)_y-(W-O)_w-R_x$$

wherein the symbols $Y_1$, y, W, w and $R_x$ have the meanings as defined in the following, linked as substituents on their aromatic ring, are endowed with a very high acaricidal activity, higher than of the compounds known from the prior art, in which saids radicals do not contain halogen atoms.

Therefore, the object of the instant invention are novel pyridazinones having the general formula (I):

(I)

wherein:

R represents a linear or branched ($C_2$-$C_6$) alkyl radical; a phenyl radical possibly substituted by halogen atoms, lower alkyl, haloalkyl, alkoxy, haloalkoxy radicals;

X represents a halogen atom;

Y represents an oxygen atom or a sulfur atom, or an NH radical;

B represents:

$$-\overset{R_3}{\underset{R_4}{C}}-;$$

b is either 0 or 1;

$R_1$, $R_2$, $R_3$ and $R_4$ represent, independently from each other, H, a linear or branched ($C_1$-$C_4$) alkyl or haloalkyl radical;

Z represents a CH radical or an N atom;

$Y_1$ represents O, S, CO or $$-\overset{R_k}{\underset{R_j}{C}}-O$$

wherein:

$R_k$ and $R_j$ are, independently from each other: H, a linear or branched ($C_1$-$C_4$) alkyl or haloalkyl radical;

W represents a linear or branched ($C_2$-$C_6$) haloalkylene;

y and w are, independently from each other, either 0 or 1;

$R_x$ represents, when w=0, a linear or branched ($C_2$-$C_6$) haloalkenyl radical possibly containing a $C_1$-$C_3$ haloalcoxy or a phenyl group as a substituent, which phenyl group possibly contains its turn substituents consisting of halogen atoms, ($C_1$-$C_6$) alkyl, haloalkyl, alkoxy, haloalkoxy radicals; a ($C_3$-$C_6$) halocycloalkyl radical or a ($C_4$-$C_7$) halocycloalkylalkyl radical, which radicals can contain substituents consisting of ($C_1$-$C_4$) alkyl or haloalkyl groups; $R_x$, when w=1, represents a linear or branched ($C_1$-$C_6$) haloalkyl radical;

R' represents a halogen atom;

n is 0, 1, 2;

when n is 2 the R' radicals can be either equal to, or different from, one another.

Advantageous results were obtained by means of the use of compounds having the formula (Ia):

(Ia)

wherein:

R represents a ($C_2$-$C_6$) alkyl radical;

X represents a halogen;

Y represents O, S;

and the other symbols have the same meaning as defined hereinabove.

Such compounds are endowed with a noticeably high insecticidal and acaricidal activity against harmful insects and mites in the agricultural, civil and zootechnical fields; in particular, they are active against important species of Hemiptera, Lepidoptera, Coleoptera, Dipterans, Blattidae, Tetranychidae, Ixodides.

The compounds having the general formula (I) can be prepared by reacting a pyridazinone of formula (II) with a compound of formula (III) according to the reaction scheme (1):

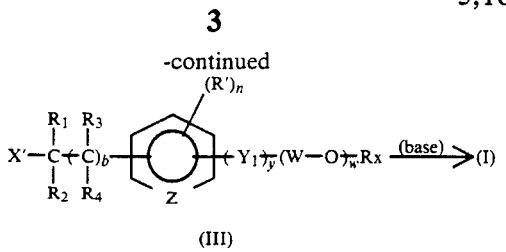

(III)

In these formulae the symbols R, X, Y, $R_1$, $R_2$, $R_3$, $R_4$, Z, $Y_1$, W, $R_x$, R', b, y, w, and n have the same meanings as hereinabove disclosed; X' and X" represent a Cl, Br or I atom, or an YH radical, in which Y has the same meaning as hereinabove defined, with the proviso that either of them should be constituted by an YH radical, and the other one should be constituted by Cl, Br, or I.

The reaction is preferably carried out in an inert organic solvent such as, e.g., benzene, toluene, acetone, methyl-ethyl-ketone, acetonitrile, dioxane, N,N-dimethylformamide, dimethyl-sulfoxide, in the presence of an inorganic base, such as, e.g., sodium hydride, sodium hydroxide, potassium hydroxide, calcium hydroxide, sodium carbonate, potassium carbonate; or of an organic base, such as, e.g., trietylamine or pyridine, at a temperature comprised within the range of from room temperature to the boiling temperature of the solvent used in the reaction.

The compounds of formula (II) are described in technical literature: they can be prepared according to as reported, e.g., on "Advances in Heterocyclic Chemistry", vol. 9, pages 235-236 and 249-258, A. R. Katritzky, A. J. Boulton Editors, Academic Press, New York and London 1968, and in therein quoted references.

The intermediates of formula (III), when are not per se known, can be prepared by using methodologies falling within the normal practice of organic chemistry.

The compounds of general formula (I) can be mixtures of isomers whose separation can be carried out by using well known chemical techniques, such as column chromatography or thin-layer chromatography.

The isolation and the use of each individual isomer, as well as the direct use of the mixtures which can be obtained from the preparation of the compounds, and the use of the mixtures deriving from an incomplete separation of the isomers fall within the scope of the instant invention.

As mentioned in the foregoing, the compounds of general formula (I) are in particular endowed with high insecticidal and acaricidal activity, which is shown in general at all of the stages of the life cycle of insects and mites larvae adult insects and eggs); they display a wide range of action and an excellent residual activity.

Thanks to their positive characteristics, the compounds of formula (I) are suitable for use in defending from harmful insects and mites both cultivations of agricultural and horticultural interest, and premises where man and domestic animals and breeding animals go often to.

For the purposes of their practical use, both in agriculture and in other sectors, the compounds according to the present invention are advantageously used in the form of suitable compositions.

These compositions contain, besides one or more compound(s) of formula (I) as their active principle, inert, solid vehicles (such as, e.g., kaolin, silica, talc, attapulgite, bentonite, diatomaceous earth, and so forth); or liquid vehicles (organic solvents, vegetable or mineral oils, water and their mixtures) and, possibly, further additives as normally used in the formulative field, such as surfactants, suspending agents, dispersing agents and wetting agents.

For special application requirements or in order to extend the range of action of the compositions, to said compositions further active ingredients can be added, such as, e.g., other insecticides or acaricides, herbicides, fungicides or fertilizers.

The application dosages vary as a function of several factors, among which the type and level of infestation, the type of composition used, climatic and environmental factors, can be reminded.

For the uses in the agricultural practice, doses of the compound of formula (I) comprised within the range of from 5 g to 5 kg per hectare supply a high enough protection.

The following examples are supplied for the purpose of better illustrating the invention.

EXAMPLE 1

Synthesis of 4-(1,1,2-trifluoro-2-trifluoromethoxy-ethoxy)-α-methylbenzyl alcohol [intermediate of formula (III)]

13.6 g of 4-hydroxyacetophenone (100 mmol), 5.6 g of ground potassium hydroxide, 120 cc of toluene, 30 cc of dimethyl-sulfoxide are charged to a flask of 250 ml of capacity.

The flask is evacuated and 16.6 g (100 mmol) of perfluorovinylether ($CF_3OCF=CF_2$) is bubbled through the reaction mixture, with the temperature being constantly kept at 20° C.

At the end of the bubbling step, the reaction mixture is acidified, is extracted with ether and is washed with brine. The ether phases are thoroughly dehydrated with sodium sulfate and are evaporated to dryness on a rotary evaporator ("rotavapor"). The so obtained raw reaction product (25 g) is dissolved in 200 cc of anhydrous ethanol. The solution is cooled to 0° C. and 3.8 g of sodium boronhydride is added portionwise.

The solution is left standing at room temperature and 30 minutes later it is neutralized with a saturated solution of ammonium chloride and is extracted with ether. The ether phases are thoroughly dried, evaporated to dryness and the residues are chromatographed on silica gel, with a 9:1 mixture of hexane/ethyl acetate being used as the eluent. The eluate is then distilled under vacuum (b.p. 74°-79° C. under 0.2 $mm_{Hg}$).

18.3 g of pure product is obtained.

N.M.R. (60 MHz, $CDCl_3$): 1.2 (d. 3H); 3.15 (s. 1H); 4.65 (q. 1H); 5.9 (dt 1H); 7.25 (ab q. 4H).

EXAMPLE 2

Synthesis of 4-(1,1,2-trifluoro-2-trifluoromethoxy-ethoxy)-α-methylbenzyl bromide [Intermediate of formula (III)]

3 g of 4-(1,1,2-trifluoro-2-trifluoromethoxy-ethoxy)-α-methylbenzyl alcohol (prepared as disclosed in Example 1) is dissolved in 20 cc of anhydrous ether and the solution is cooled down to −70° C. Then, 0.4 cc of $PBr_3$ is added to the mixture.

The reaction mixture is left standing at room temperature and 30 minutes later a saturated solution of sodium bicarbonate is added to it. The reaction mixture is extracted with ether and the ether phases are washed with water up to neutral. The ether phases are thoroughly dried, are concentrated to dryness by means of the rotovapor and are chromatographed on silica gel with a 95/5 mixture of hexane/ethyl acetate, with 2.2 g of pure product being obtained.

N.M.R. (60 MHz, CDCl$_3$): 1.2 (d. 3H); 4.5 (q. 1H); 5.9 (dt 1H); 7.25 (ab q. 4H).

EXAMPLE 3

Synthesis of 4-(1,1,2-trifluoro-2-trifluoromethoxy-ethoxy)-benzyl alcohol [Intermediate of formula (III)]

12.4 g of 4-hydroxybenzaldehyde (100 mmol), 5.6 g of ground potassium hydroxide, 120 cc of toluene, 30 cc of dimethyl-sulfoxide are charged to a flask of 250 ml of capacity.

The flask is evacuated and 16.6 g (100 mmol) of perfluoromethylvinylether (CF$_3$OCF=CF$_2$) is bubbled through the reaction mixture, with the temperature being kept constant at 20° C.

At the end of the bubbling step, the reaction mixture is acidified, is extracted with ether and is washed with brine. The ether phases are thoroughly dried with sodium sulfate and are concentrated to dryness on the rotavapor. The so obtained raw reaction product (24 g) is dissolved in 200 cc of anhydrous ethanol. The solution is cooled to 0° C. and 3.8 g of sodium borohydride is added portionwise.

The solution is left standing at room temperature and 30 minutes later it is neutralized with a saturated solution of ammonium chloride and is extracted with ether. The ether phases are thoroughly dried, are evaporated and are chromatographed on silica gel, with a 9:1 mixture of hexane/ethyl acetate being used as the eluent. The eluate is then distilled under vacuum (b.p. 83° C. under 0.3 mm$_{Hg}$).

14.3 g of pure product is obtained.

N.M.R. (60 MHz, CDCl$_3$): 3.15 (s. 1H); 4.65 (s. 1H); 5.9 (dt 1H); 7.25 (ab q. 4H).

EXAMPLE 4

Synthesis of 4-(1,1,2-trifluoro-2-trifluoromethoxy-ethoxy)-benzyl bromide [Intermediate of formula (III)]

3 g of 4-(1,1,2-trifluoro-2-trifluoromethoxy-ethoxy)-benzyl alcohol (prepared as disclosed in Example 3) is dissolved in 20 cc of anhydrous ether and the solution is cooled down to −70° C. Then, 0.4 cc of PBr$_3$ is added to the mixture.

The reaction mixture is left standing at room temperature and 30 minutes later a saturated solution of sodium bicarbonate is added to it. The reaction mixture is extracted with ether and the ether phases are washed with water up to neutral. The ether phases are thoroughly dried, are concentrated to dryness on the rotovapor and are chromatographed on silica gel with a 95/5 mixture of hexane/ethyl acetate, with 2.2 g of pure product being obtained.

N.M.R. (60 MHz, CDCl$_3$): 4.4 (s. 2H); 5.9 (dt 1H); 7.3 (ab q. 4H).

EXAMPLE 5

Synthesis of 4-(2-chloro-3,3,3-trifluoroprop-1-enyl)-benzyl bromide [intermediate of formula (III)]

12 g of p-tolualdehyde dissolved in 20 cc of DMF and 7.5 g of Zn are charged to a flask of 250 ml of capacity. 2.5 g of CF$_3$CCl$_3$ is dropwise added and the resulting reaction mixture is slightly heated until the reaction turns into strongly exothermic. Then 10 g of CF$_3$CCl$_3$ dissolved in 100 cc of DMF is dropwise added and the resulting mixture is stirred at room temperature for 4 hours. 10 cc of acetic anhydride and 13 g of Zn are then added. After 2 hours at room temperature, the reaction mixture is poured in acidic water and is extracted three times with ether; the ether phases are combined with one another, and are washed with a saturated solution of sodium bicarbonate, and with brine, and are then thoroughly dried and evaporated. The raw reaction product is chromatographed on silica (98/2 hexane/ethyl acetate). 11.5 g of 4-(2-chloro-3,3,3-trifluoroprop-1-enyl)-toluene is obtained.

The obtained product is dissolved in 120 cc of CCl$_4$, 10.8 g of N-bromo-succinimide and 0.5 g of benzoyl peroxide are added. The resulting mixture is stirred under refluxing conditions for 2 hours, is diluted with hexane, is filtered and evaporated. The raw reaction product is chromatographed on silica (99/1 hexane/ethyl acetate), and 9 g of product is obtained.

N.M.R. (60 MHz, CDCl$_3$): 4.5 (s. 2H); 7.85–7.3 (m. 5H).

EXAMPLE 6

Synthesis of 2-tert.-butyl-4-chloro-5-[4-(1,1,2-trifluoro-2-trifluoromethoxy-ethoxy)-α-methyl-benzyloxy]-3(2H)-pyridazinone [Compound (1)]

1.5 g of 4-(1,1,2-trifluoromethoxy-ethoxy)-α-methylbenzyl alcohol (Example 1) is added to a suspension of 0.24 g of sodium hydride at 50% in 10 cc of formaldehyde and 15 minutes later 1.1 g of 2-tert.-butyl-4,5-dichloro-3(2H)-pyridazinone is added to the resulting mixture. The reaction mixture is stirred for 1 hour at room temperature, is diluted with ether, is washed with diluted HCl and brine; the washed solution is thoroughly dehydrated, the solvent is evaporated off and the so obtained raw reaction product is chromatographed on silica gel with 9/1 hexane/ethyl acetate. 0.9 g of pure product is obtained.

N.M.R. (60 MHz CDCl$_3$): 1.6 (s. 9H); 1.75 (d 3H); 5.5 (q 1H); 6.0 (tt 1H); 7.3 (ab q 4H); 7.5 (s 1H).

EXAMPLE 7

Synthesis of 2-tert.-butyl-4-chloro-5-[4-(1,1,2-trifluoro-2-trifluoromethoxy-ethoxy)-α-methylbenzylthio]-3(2H)-pyridazinone [Compound (2)]

1.4 g of 4-(1,1,2-trifluoro-2-trifluoromethoxy-ethoxy)-α-methyl-benzyl bromide (Example 2) and 1 g of 2-tert.-butyl-4-chloro-5-mercapto-3(2H)-pyridazinone are added to a suspension of 0.8 g of potassium carbonate in 10 cc of dimethylformamide. The resulting reaction mixture is stirred for 1 hour at room temperature, is diluted with ether, is washed with diluted HCl and brine; the washed solution is thoroughly dehydrated, the solvent is evaporated off and the so obtained raw reaction product is chromatographed on silica gel with 9/1 hexane/ethyl acetate. 0.58 g of pure product is obtained.

N.M.R. (60 MHz CDCl$_3$): 1.6 (s. 9H); 1.75 (d 3H); 4.75 (q 1H); 6.0 (tt 1H); 7.4 (ab q 4H); 7.5 (s 1H).

EXAMPLE 8

Synthesis of 2-tert.-butyl-4-chloro-5-[4-(1,1,2-trifluoro-2-trifluoromethoxy-ethoxy)-benzyloxy]-3(2H)-pyridazinone [Compound (3)]

1.16 g of 4-(1,1,2-trifluoro-2-trifluoromethoxy-ethoxy)-benzyl alcohol (Example 3) and, 15 minutes later, 0.95 g of 2-tert.-butyl-4,5-dichloro-3(2H)-pyridazinone are added to a suspension of 0.2 g of sodium hydride at 50% in 10 cc of dimethylformamide. The resulting reaction mixture is stirred for 1 hour at room temperature, is diluted with ether, is washed with diluted HCl and brine; the washed solution is thoroughly dehydrated, the solvent is evaporated off and the so obtained raw reaction product is chromatographed on silica gel with 9/1 hexane/ethyl acetate. 1.3 g of pure product is obtained. Melting point 68°–69° C.

N.M.R. (60 MHz CDCl$_3$): 1.65 (s. 9H); 5.5 (d 2H); 6.1 (tt 1H); 7.5 (ab q 4H); 7.9 (s 1H).

EXAMPLE 9

Synthesis of 2-tert.-butyl-4-chloro-5-[4-(1,1,2-trifluoro-2-trifluoromethoxyethoxy)-benzylthio]-3(2H)-pyridazinone [Compound (4)]

1.4 g of 4-(1,1,2-trifluoro-2-trifluoromethoxy-ethoxy)-benzyl bromide (Example 4) and 1 g of 2-tert.-butyl-4-chloro-5-mercapto-3(2H)-pyridazinone are added to a suspension of 0.8 g of potassium carbonate in 10 cc of dimethylformamide. The resulting reaction mixture is stirred for 1 hour at room temperature, is diluted with ether, is washed with diluted HCl and brine; the washed solution is thoroughly dehydrated, the solvent is evaporated off and the so obtained raw reaction product is chromatographed on silica gel with 9/1 hexane/ethyl acetate. 1.4 g of pure product is obtained.

N.M.R. (60 MHz CDCl$_3$): 1.6 (s. 9H); 4.75 (s 2H); 6.0 (tt 1H); 7.4 (bs 4H); 7.5 (s 1H).

EXAMPLE 10

Synthesis of 2-tert.-butyl-4-chloro-5-[4-(2-chloro-3,3,3-trifluoroprop-1-enyl)-benzyl-thio]-3(2H)-pyridazinone [Compound 10]

1.2 g of 4-(2-chloro-3,3,3-trifluoroprop-1-enyl)-benzyl bromide and 0.8 g of 2-tert.-butyl-4-chloro-5-mercapto-3(2H)-pyridazinone are added to a suspension of 0.7 g of potassium carbonate in 10 cc of dimethylformamide.

The resulting reaction mixture is stirred for 1 hour at room temperature, is diluted with ether, is washed with diluted HCl and brine; the washed solution is thoroughly dehydrated, the solvent is evaporated off and the so obtained raw reaction product is chromatographed on silica gel with 9/1 hexane/ethyl acetate. 0.9 g of pure product is obtained. Melting point = 124° C.

N.M.R. (60 MHz CDCl$_3$): 1.6 (s. 9H); 4.25 (s 2H); 6.75 (s 1H); 7.6–7.2 (m 5H).

EXAMPLE 11

Synthesis of 2-tert.-butyl-4-chloro-5-[4-(2,2-dichloroethenyl)-benzylthio]-3(2H)-pyridazinone [Compound (11)]

1.2 g of 4-(2,2-dichloroethenyl)-benzyl bromide and 0.8 g of 2-tert.-butyl-4-chloro-5-mercapto-3(2H)-pyridazinone are added to a suspension of 0.7 g of potassium carbonate in 10 cc of dimethylformamide.

The resulting reaction mixture is stirred for 1 hour at room temperature, is diluted with ether, is washed with diluted HCl and brine; the washed solution is thoroughly dehydrated, the solvent is evaporated off and the so obtained raw reaction product is chromatographed on silica gel with 9/1 hexane/ethyl acetate. 1.13 g of pure product is obtained. Melting point = 105° C.

N.M.R. (60 MHz CDCl$_3$): 1.6 (s 9H); 4.25 (s 2H); 7.6–7.0 (m. 6H).

By operating in the same way as disclosed in the Examples from 6 to 11, the compounds reported in Table 1 were obtained.

In such Table are also reported four reference compounds which fall within the EPA 199281: the reference compounds are identified as follows: RC$_1$; RC$_2$; RC$_3$; RC$_4$.

TABLE 1

| Comp. | R | X | Y | $\begin{array}{c} R_1\ R_3 \\ C-(C) \\ R_2\ R_4 \end{array}$ | Z | (R')$_n$ | Rx—(O—W)$_w$(Y$_1$)$_y$ | m.p. |
|---|---|---|---|---|---|---|---|---|
| 1 | t-Bu | Cl | O | Me—CH | CH | — | 4-CF$_3$OCFHCF$_2$O | |
| 2 | t-Bu | Cl | S | Me—CH | CH | — | " | |
| 3 | t-Bu | Cl | O | CH$_2$ | CH | — | " | 68–9 |
| 4 | t-Bu | Cl | S | CH$_2$ | CH | — | " | 98 |

TABLE 1-continued

| Comp. | R | X | Y | $\begin{array}{c}R_1\;R_3\\|\;\;|\\C-(C)\\|\;\;|\\R_2\;R_4\end{array}$ | Z | (R')$_n$ | Rx—(O—W)$_w$(Y$_1$)$_y$ | m.p. |
|---|---|---|---|---|---|---|---|---|
| 5 | t-Bu | Cl | S | CH$_2$ | CH | — | 4-CF$_3$CF$_2$OCFHCF$_2$O | 88 |
| 6 | t-Bu | Cl | S | Me\|CH | " | — | " | |
| 7 | t-Bu | Cl | S | CH$_2$ | CH | — | 4-CF$_3$OCFHCF$_2$S | 88 |
| 8 | t-Bu | Cl | S | CH$_2$ | CH | — | 4-CF$_3$OCFHCF$_2$OCH(Me) | 57-9 |
| 9 | t-Bu | Cl | S | CH$_2$ | CH | — | 4-CF$_3$OCFHCF$_2$OCH(CF$_3$) | 73-5 |
| 10 | t-Bu | Cl | S | CH$_2$ | CH | — | 4-CF$_3$C(Cl)=CH | 123-5 |
| 11 | t-Bu | Cl | S | CH$_2$ | CH | — | 4-Cl$_2$C=CH | 104-6 |
| 12 | t-Bu | Cl | S | CH$_2$ | CH | — | 4-CF$_3$C(F)=CH | 87-9 |
| 13 | t-Bu | Cl | S | CH$_2$ | CH | — | 4-CF$_3$C(F)=CF | 100-2 |
| 14 | t-Bu | Cl | S | CH$_2$ | CH | — | 4-CF$_3$OCF=CF | 81 |
| 15 | t-Bu | Cl | S | CH$_2$ | CH | — | 4-CF$_3$CF$_2$OCF=CF | 70-2 |
| 16 | t-Bu | Cl | S | Me\|CH | CH | — | 4-CF$_3$C(Cl)=CH | |
| 17 | t-Bu | Cl | S | Me\|CH | CH | — | 4-Cl$_2$C=CH | |
| 18 | t-Bu | Cl | S | Me\|CH | CH | — | 4-CF$_3$OCF=CF | |
| 19 | t-Bu | Cl | S | CH$_2$ | CH | — | 4-PhC(Cl)=CH | |
| 20 | t-Bu | Cl | S | CH$_2$ | CH | — | 4-(p-ClPh)C(Cl)=CH | |
| 21 | t-Bu | Cl | S | CH$_2$ | CH | 3-Cl | 4-CF$_3$OCFHCF$_2$O | 76 |
| 22 | t-Bu | Cl | S | CH$_2$ | CH | 3,5-Cl$_2$ | 4-CF$_3$OCFHCF$_2$O | 98 |
| 23 | t-Bu | Cl | S | CH$_2$ | CH | 3-F | " | 97 |
| 24 | t-Bu | Cl | S | CH$_2$ | CH | 2-F | " | 74 |
| 25 | t-Bu | Cl | S | CH$_2$CH$_2$ | CH | — | " | |
| 26 | t-Bu | Cl | O | " | CH | — | " | |
| 27 | t-Bu | Cl | NH | CH$_2$ | CH | — | " | |
| 28 | t-Bu | Cl | S | 2-CH$_2$ | N | — | 5-CF$_3$OCFHCF$_2$O | |
| 29 | t-Bu | Cl | S | CH$_2$ | CH | — | 4-(CH$_3$)$_2$C—CH (CCl$_2$ bridge, cyclopropane) | 140 |
| 30 | t-Bu | Cl | S | CH$_2$ | CH | — | 4-CH$_3$CH—CH (CCl$_2$ bridge, cyclopropane) | |

TABLE 1-continued

Structure:
R-N(N=)C(=O)-C(X)=C(Y-CR1R2-C(R3R4)(-phenyl with (R')n and Z)-Y1y-(W-O)w-Rx)

| Comp. | R | X | Y | R1,R2 / C | R3,R4 / (C) | Z | (R')n | Rx—(O—W)w(Y1)y | m.p. |
|---|---|---|---|---|---|---|---|---|---|
| 31 | t-Bu | Cl | S | CH2 | | CH | — | 4-Cl2C—C(CH3)CH2O (with CH2 bridge, cyclopropane) | |
| 32 | t-Bu | Cl | S | CH2 | | CH | — | 4-Cl2C—C(CH3)CO (with CH bridge, cyclopropane) | 161 |
| 33 | 3,4-diCl-phenyl | Cl | O | CH2 | | CH | — | 4-CF3OCFHCF2O | |
| 34 | 3,4-diCl-phenyl | Cl | S | CH2 | | CH | — | " | |
| 35 | 2-Cl-phenyl | Cl | O | CH2 | | CH | — | " | |
| 36 | 2-Cl-phenyl | Cl | S | " | | " | — | " | |
| 37 | 2,6-diCl-phenyl | Cl | O | " | | " | — | " | |
| 38 | 2,6-diCl-phenyl | Cl | S | " | | " | — | " | |
| 39 | 2,6-diF-phenyl | Cl | O | " | | " | — | " | |

TABLE 1-continued

Structure:
$$\underset{R_2\ R_4}{\underset{|\ \ |}{R}\underset{}{\overset{O}{\underset{\|}{\underset{N}{\overset{}{\underset{|}{N}}}}}\underset{}{\overset{X}{\underset{}{\ }}}\ Y-\underset{R_2}{\underset{|}{C}}-(\underset{R_4}{\underset{|}{C}})\underset{Z}{\ }\underset{}{\phi(R')_n}-(Y_1)_y-(W-O)_w-R_x}}$$

|       |       |       |       | $\begin{array}{cc} R_1 & R_3 \\ | & | \\ C-(C) \\ | & | \end{array}$ |       |       |                  |      |
|-------|-------|-------|-------|-------|-------|-------|------------------|------|
| Comp. | R     | X     | Y     | $R_2\ R_4$ | Z | $(R')_n$ | $R_x-(O-W)_w(Y_1)_y$ | m.p. |
| 40    | ![2,6-difluorophenyl] | F, F phenyl | Cl | S | " | " | — | " |         |
| $RC_1$ | t-Bu | Cl | O | Me\|CH | CH | — | 4-CH$_3$OCH$_2$CH$_2$O |   |
| $RC_2$ | t-Bu | Cl | S | Me\|CH | CH | — | " |   |
| $RC_3$ | t-Bu | Cl | O | CH$_2$ | CH | — | " |   |
| $RC_4$ | t-Bu | Cl | S | CH$_2$ | CH | — | " |   |

EXAMPLE 12

Determination of the insecticidal and acaricidal activity a) Insecticidal activity against adults of *Macrosiphum euphorbiae* (M.E.; aphids)

Small potato plants grown in pot were infested with adult female aphids and, a few hours later, onto them a suspension in water-acetone (acetone at 10% by volume) of the product being tested was sprayed.

24 hours after the treatment the percent mortality rate of the aphids was determined, as compared to the mortality rate of aphids infesting plants only treated with a solution of 10% of acetone in water.

b) Insecticidal activity against eggs and larvae of *Leptinotarsa decemlineata* (L.D.; coleoptera)

Potato leaves on which living eggs of the coleopter had been laid during the preceding 24 hours, were dipped in water-acetone solutions (at 10% by volume of acetone) of the tested product. The leaves were then placed on humidified filter papers.

6 days after the treatment the percent number of not opened eggs and of dead larvae was detected, vs. the percent number of eggs and larvae infesting leaves treated with the only water solution at 10% of acetone.

c) Acaricidal activity against *Tetranychus urticae* (T.U.; mites)

Adult mites

Small disks obtained from bean leaves were infested with adult mites and onto them a water-acetone solution (acetone 10% by volume) of the tested product was then sprayed.

The percent rate of mortality was determined after 48 hours of treatment, as compared to that of mites infesting disks onto which only an aqueous solution at 10% of acetone was sprayed.

Eggs

Disks obtained from bean leaves were infested with eggs of the mite, and after the disks were treated by being sprayed with a water-acetone solution of the tested product.

The percent number of not opened eggs was evaluated after 7 days after the treatment, as compared to the percent number of eggs only treated with the water-acetone mixture.

Larvae

Small disks obtained from bean leaves were infested with eggs of the mite. 24 hours after the complete opening of the eggs, the juvenile forms of the mite were treated by being sprayed with a water-acetone solution of the tested product.

The percent rate of mortality of the larvae was determined 72 hours after the treatment, as compared to that of larvae infesting disks onto which only a water-acetone solution was sprayed.

By operating according to the hereinabove disclosed modalities, the compounds according to the invention were tested in order to determine their insecticidal and acaricidal activity.

The results of the determinations carried out are reported in Table 2. Such results are expressed as the percent rate of mortality of the insects and mites treated with the tested compounds, at the set forth doses.

TABLE 2

| Compound | M.E. 100 ppm | L.D. 1000 ppm | T.U. adults 10 ppm | T.U. eggs 10 ppm |
|----------|--------------|---------------|--------------------|-----|
| 1 | 100 | 100 | 100 | 100 |
| 2 | 100 | 100 | 100 | 100 |
| 3 | 100 | 100 | 100 | 100 |
| 4 | 100 | 100 | 100 | 100 |
| 5 | 100 | n.t. | 100 | 100 |
| 6 | 100 | n.t. | 100 | 100 |
| 7 | 100 | 100 | 100 | 100 |

TABLE 2-continued

| Compound | M.E. 100 ppm | L.D. 1000 ppm | T.U. adults 10 ppm | T.U. eggs 10 ppm |
|---|---|---|---|---|
| 8 | 100 | 100 | 100 | 100 |
| 9 | 96 | 100 | 100 | 100 |
| 10 | 100 | 100 | 100 | 100 |
| 11 | 100 | 100 | 100 | 100 |
| 12 | 100 | 100 | 100 | 100 |
| 13 | 100 | 100 | 100 | 100 |
| 14 | 100 | 100 | 100 | 100 |
| 15 | 90 | 100 | 100 | 100 |
| 16 | 100 | 100 | 100 | 100 |
| 17 | 100 | 100 | 100 | 100 |
| 18 | 100 | 100 | 100 | 100 |
| 21 | 100 | 100 | 100 | 100 |
| 22 | 100 | 100 · | 100 | 95 |
| 23 | 100 | 100 | 100 | 100 |
| 30 | 100 | 100 | 100 | 100 | nt = not tested

In Table 3 are reported the data of acaricidal activity (adults, eggs, larvae) of compounds 1 to 4 in comparison with the data of acaricidal activity of the reference compounds $RC_1$ to $RC_4$ of the European patent application 199281.

TABLE 3

| Compound | T.U. adults 10 ppm 1 ppm 0.1 ppm | T.U. eggs 10 ppm 1 ppm 0.1 ppm | T.U. larvae 10 ppm 1 ppm 0.1 ppm |
|---|---|---|---|
| 1 | 100 | 100 | 98 |
|   | 42 | 54 | 90 |
|   | nt | nt | 41 |
| $RC_1$ | 18 | 22 | 18 |
|   | 7 | 10 | 9 |
|   | nt | nt | nt |
| 2 | 100 | 100 | 100 |
|   | 100 | 100 | 100 |
|   | 90 | 95 | 100 |
| $RC_2$ | 100 | 100 | 100 |
|   | 100 | 98 | 98 |
|   | 13 | 6 | 70 |
| 3 | 100 | 100 | 100 |
|   | 71 | 90 | 85 |
|   | nt | nt | 53 |
| $RC_3$ | 7 | 77 | 33 |
|   | 0 | 24 | 0 |
|   | nt | nt | nt |
| 4 | 100 | 100 | 100 |
|   | 90 | 100 | 100 |
|   | 70 | 65 | 100 |
| $RC_4$ | 80 | 100 | 100 |
|   | 42 | 90 | 96 |
|   | 4 | 55 | 32 |

What is claimed is:

1. Pyridazinones having the formula (I):

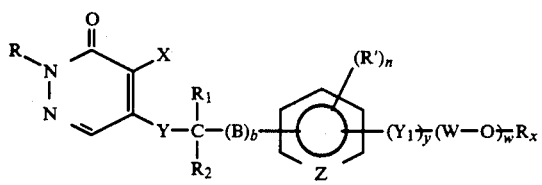

(I)

wherein:
R represents a linear or branched ($C_2$-$C_6$) alkyl radical;
X represents halogen;
Y represents oxygen, sulfur or an NH radical;
B represents:

b is either 0 or 1;
$R_1$, $R_2$, $R_3$ and $R_4$ represent, independently from each other, H, a linear or branched ($C_1$-$C_4$) alkyl or haloalkyl radical;
Z represents a CH radical;
$Y_1$ represents O, S, CO or

wherein:
$R_k$ and $R_j$ are, independently from each other: H, a linear or branched ($C_1$-$C_4$) alkyl or haloalkyl radical;
W represents a linear or branched ($C_2$-$C_6$) haloalkylene;
y and w are, independently from each other, either 0 or 1;
$R_x$ represents, when w=0, a linear or branched ($C_2$-$C_6$) haloalkenyl radical having a $C_1$-$C_3$ haloalkoxy or a phenyl group as a substituent, which phenyl group is unsubstituted or substituted by halogen, ($C_1$-$C_6$) alkyl, haloalkyl, alkoxy, or haloalkoxy radicals; a ($C_3$-$C_6$) halocycloalkyl radical or a ($C_4$-$C_7$) halocycloalkylalkyl radical, which radicals can have substituents consisting of ($C_1$-$C_4$) alkyl or haloalkyl groups; $R_x$, when w=1, represents a linear or branched ($C_1$-$C_6$) haloalkyl radical;
R' represents halogen;
n is 0, 1, or 2; when n is 2, the R' radicals can be either equal to, or different from, one another.

2. Pyridazinones according to claim 1 having the formula:

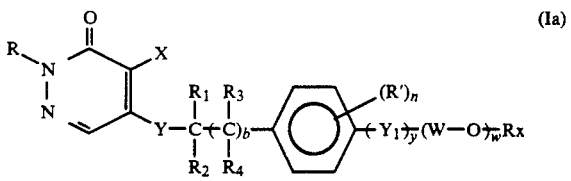

(Ia)

wherein:
R represents a ($C_2$-$C_6$) alkyl radical;
X represents a halogen atom;
Y represents O, S;
and the other symbols have the same meaning as defined in claim 1.

3. 2-tert.-butyl-4-chloro-5-[4-(1,1,2-trifluoro-2-trifluoromethoxy-ethoxy)-α-methyl-benzyloxy]-3(2H)-pyridazinone.

4. 2-tert.-butyl-4-chloro-5-[4-(1,1,2-trifluoro-2-trifluoromethoxy-ethoxy)-α-methyl-benzylthio]-3(2H)-pyridazinone.

5. 2-tert.-butyl-4-chloro-5-[4-(1,1,2-trifluoro-2-trifluoromethoxy-ethoxy)-benzyloxy]-3(2H)-pyridazinone.

6. 2-tert.-butyl-4-chloro-5-[4-(1,1,2-trifluoro-2-trifluoromethoxy-ethoxy)-benzylthio]-3(2H)-pyridazinone.

7. 2-tert.-butyl-4-chloro-5-[4-(2-pentafluoroethoxy-1,1,2-trifluoroethoxy)-benzylthio]-3(2H)-pyridazinone.

8. 2-tert.-butyl-4-chloro-5-[4-(2-pentafluoroethoxy-1,1,2-trifluoro-ethoxy)α-methylbenzylthio]-3(2H)-pyridazinone.

9. 2-tert.-butyl-4-chloro-5-[4-(2-chloro-3,3,3-trifluoropropenyl)-benzylthio]-3(2H)-pyridazinone.

10. 2-tert.-butyl-4-chloro-5-[4-2,2-dichloro-ethenyl)-benzylthio]-3(2H)-pyridazinone.

11. 2-tert.-butyl-4-chloro-5-[4-(1,1,2-trifluoro-2-trifluoromethoxy-ethoxy)-ethyl)-benzylthio]-3(2H)-pyridazinone.

12. 2-tert.-butyl-4-chloro-5-[4-(1,2-difluoro-2-trifluoromethoxy-ethenyl)-benzylthio]-3(2H)-pyridazinone.

13. 2-tert.-butyl-4-chloro-5-[4-(2-chloro-3,3,3-trifluoropropenyl)-α-methylbenzylthio]-3(2H)-pyridazinone.

14. 2-tert.-butyl-4-chloro-5-[4-(2,2-dichloroethenyl)-α-methyl-benzylthio]-3(2H)-pyridazinone.

15. 2-tert.-butyl-4-chloro-5-[4-(1,2-difluoro-2-trifluoromethoxy-ethenyl)-α-methylbenzylthio]-3(2H)-pyridazinone.

16. 2-tert.-butyl-4-chloro-5-[4-(2-chloro-2-phenylethenyl)-benzylthio]-3(2H)-pyridazinone.

17. 2-tert.-butyl-4-chloro-5-[4-(2-chloro-(4-chlorophenyl)-ethenyl)-benzylthio]-3(2H)-pyridazinone.

18. 2-tert.-butyl-4-chloro-5-[4-(2,2-dichloro-1-methyl-cyclopropyl-methoxy)-benzylthio]-3(2H)-pyridazinone.

19. 2-tert.-butyl-4-chloro-5-[4-(2,2-dichloro-1-methyl-cyclopropyl-carbonyl)-benzylthio]-3(2H)-pyridazinone.

20. 2-(3,4-dichlorophenyl)-4-chloro-5-[4-(1,1,2-trifluoro-2-trifluoromethoxy-ethoxy)-benzyloxy]-3(2H)-pyridazinone.

21. 2-(3,4-dichlorophenyl)-4-chloro-5-[4-(1,1,2-trifluoro-2-trifluoromethoxy-ethoxy)-benzylthio]-3(2H)-pyridazinone.

22. A compound having the structure

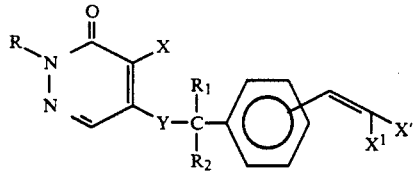

wherein;
R is branched $C_2$–$C_6$ alkyl;
X is halogen;
Y is oxygen or sulfur;
$R_1$ and $R_2$ are independently H or lower linear alkyl;
$X^1$ is halogen.

23. A compound having the structure as recited in claim 22, wherein Y is sulfur.

24. A compound having the structure as recited in claim 22 wherein X is chlorine.

25. A compound having the structure as recited in claim 24 wherein each $X^1$ is chlorine.

26. Method for fighting infestations by harmful mites, insects or a combination thereof in agricultural cultivations, horticultural cultivations or in premises where man, domestic animals, breeding animals or a combination thereof go often to, consisting in applying to the cultivation or in said premises an effective amount of at least one pyridazinone having the formula (I) of claim 1.

27. Compositions for fighting infestations by harmful mites, insects or a combination thereof, characterized in that they contain, besides one or more solid or liquid carriers, as well as further additives and other active substances and fertilizers, usual in formulative field, at least one pyridazinone having formula (I) of claim 1.

* * * * *